US010420597B2

(12) United States Patent
Papangelou et al.

(10) Patent No.: US 10,420,597 B2
(45) Date of Patent: Sep. 24, 2019

(54) SURGICAL IMPLANT WITH POROUS REGION

(71) Applicant: ARTHREX, INC., Naples, FL (US)

(72) Inventors: Chris Papangelou, Bonita Springs, FL (US); G. Joshua Karnes, Estero, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 14/571,677

(22) Filed: Dec. 16, 2014

(65) Prior Publication Data

US 2016/0166301 A1    Jun. 16, 2016

(51) Int. Cl.
*A61B 17/80* (2006.01)
*A61B 17/86* (2006.01)
(Continued)

(52) U.S. Cl.
CPC ...... *A61B 17/8625* (2013.01); *A61B 17/0401* (2013.01); *A61B 17/7035* (2013.01);
(Continued)

(58) Field of Classification Search
CPC ... A61B 17/80; A61B 17/809; A61B 17/8095; A61B 17/864; A61F 2/2846; A61F 2/30907; A61F 2/4465; A61F 2002/30011; A61F 2002/30013; A61F 2002/30028; A61F 2002/30029; A61F 2002/30032; A61F 2002/30034; A61F 2002/2835; A61F 2002/285; A61F 2002/30112; A61F 2002/30113; A61F 2002/30115; A61F 2002/30125; A61F 2002/30126;
(Continued)

(56) References Cited

U.S. PATENT DOCUMENTS 5,211,664 A * 5/1993 Tepic ............... A61F 2/2846
606/60
5,360,448 A   11/1994 Thramann
(Continued)

FOREIGN PATENT DOCUMENTS

CN        101340851 A    1/2009
CN        101437569 A    5/2009
(Continued)

OTHER PUBLICATIONS

The International Search Report and Written Opinion for PCT Application No. PCT/US2015/052121, dated Nov. 19, 2015.

*Primary Examiner* — David H Willse
*Assistant Examiner* — Javier G Blanco
(74) *Attorney, Agent, or Firm* — McDonnell Boehnen Hulbert & Berghoff LLP

(57) ABSTRACT

A surgical implant according to an exemplary aspect of the present disclosure includes, among other things, a body that extends along a longitudinal axis between a drive head and a tip. The body includes a cannulation disposed about the longitudinal axis and extending from the tip to the drive head, a solid thread that wraps around the body and a porous region circumferentially extending about the body between adjacent revolutions of the solid thread. In another embodiment, the surgical implant may include a wedge having at least one porous region that extends continuously around a wedge body between an inner wall and an outer wall.

7 Claims, 7 Drawing Sheets

(51) Int. Cl.
    *A61B 17/04* (2006.01)
    *A61F 2/28* (2006.01)
    *A61F 2/08* (2006.01)
    *A61B 17/70* (2006.01)
    *A61B 17/00* (2006.01)

(52) U.S. Cl.
    CPC ........ *A61B 17/8095* (2013.01); *A61B 17/864* (2013.01); *A61B 17/866* (2013.01); *A61B 17/8615* (2013.01); *A61B 17/8645* (2013.01); *A61F 2/0811* (2013.01); *A61F 2/28* (2013.01); *A61B 2017/00964* (2013.01); *A61B 2017/044* (2013.01); *A61B 2017/0445* (2013.01); *A61B 2017/8655* (2013.01); *A61F 2002/0841* (2013.01); *A61F 2002/0858* (2013.01); *A61F 2002/0888* (2013.01); *A61F 2250/0024* (2013.01)

(58) Field of Classification Search
    CPC ...... A61F 2002/30187; A61F 2002/302; A61F 2002/30202; A61F 2002/30204; A61F 2002/30225; A61F 2002/3023; A61F 2250/0023; A61F 2250/0024; A61F 2250/0067; A61F 2250/0068; A61F 2002/30036; A61F 2002/3092; A61F 2002/3093; A61F 2/4455; A61F 2002/300231; A61F 2/447
    See application file for complete search history.

(56) References Cited

U.S. PATENT DOCUMENTS

| | | | |
|---|---|---|---|
| 5,650,108 A | 7/1997 | Nies et al. | |
| 5,856,367 A | 1/1999 | Barrows et al. | |
| 5,869,080 A | 2/1999 | McGregor et al. | |
| 5,876,452 A | 3/1999 | Athanasiou et al. | |
| 6,143,033 A * | 11/2000 | Paul | A61F 2/28 623/16.11 |
| 6,149,688 A * | 11/2000 | Brosnahan | A61F 2/28 623/23.5 |
| 6,206,924 B1 * | 3/2001 | Timm | A61F 2/28 623/17.11 |
| 6,228,111 B1 | 5/2001 | Tormala et al. | |
| 6,235,225 B1 | 5/2001 | Okada et al. | |
| 6,432,107 B1 * | 8/2002 | Ferree | A61B 17/1671 606/247 |
| 6,436,426 B1 | 8/2002 | Liao et al. | |
| 6,511,511 B1 | 1/2003 | Slivka et al. | |
| 6,527,810 B2 | 3/2003 | Johnson et al. | |
| 6,530,956 B1 * | 3/2003 | Mansmann | A61F 2/30756 623/18.11 |
| 6,626,945 B2 | 9/2003 | Simon et al. | |
| 6,840,960 B2 | 1/2005 | Bubb | |
| 7,112,222 B2 * | 9/2006 | Fraser | A61B 17/7059 606/247 |
| 7,235,079 B2 | 6/2007 | Jensen et al. | |
| 7,238,206 B2 * | 7/2007 | Lange | A61F 2/4465 623/17.11 |
| 7,241,313 B2 | 7/2007 | Unwin et al. | |
| 7,351,280 B2 * | 4/2008 | Khairoun | A61L 24/02 106/35 |
| 7,455,692 B2 * | 11/2008 | Michelson | A61F 2/28 623/17.11 |
| 7,578,851 B2 | 8/2009 | Dong et al. | |
| 7,879,109 B2 | 2/2011 | Borden et al. | |
| 7,892,265 B2 | 2/2011 | Perez-Cruet et al. | |
| 7,910,690 B2 | 3/2011 | Ringeisen et al. | |
| 7,943,677 B2 | 5/2011 | Papangelou et al. | |
| 8,119,152 B2 | 2/2012 | Shikinami | |
| 8,292,967 B2 | 10/2012 | Brown et al. | |
| 8,337,873 B2 | 12/2012 | Mao | |
| 8,383,024 B2 | 2/2013 | Morrissette et al. | |
| 8,389,588 B2 | 3/2013 | Ringeisen et al. | |
| 8,445,554 B2 | 5/2013 | Ringeisen et al. | |
| 8,475,505 B2 | 7/2013 | Nebosky et al. | |
| 8,500,843 B2 | 8/2013 | Grohowski | |
| 8,529,625 B2 | 9/2013 | Farrar et al. | |
| 8,535,357 B2 | 9/2013 | Stone et al. | |
| 8,657,827 B2 | 2/2014 | Fitz et al. | |
| 8,700,198 B2 | 4/2014 | Conway et al. | |
| 8,715,366 B2 | 5/2014 | Borden | |
| 2004/0082999 A1 * | 4/2004 | Mathys, Jr. | A61F 2/4455 623/17.11 |
| 2004/0258732 A1 * | 12/2004 | Shikinami | A61L 27/446 424/426 |
| 2005/0288795 A1 * | 12/2005 | Bagga | A61B 17/68 623/23.51 |
| 2006/0111715 A1 | 5/2006 | Jackson | |
| 2006/0241763 A1 * | 10/2006 | Paul | A61F 2/28 623/17.11 |
| 2006/0276788 A1 | 12/2006 | Berry | |
| 2007/0156240 A1 * | 7/2007 | Tsuang | A61F 2/4455 623/17.11 |
| 2007/0161985 A1 | 7/2007 | Demakas et al. | |
| 2007/0203584 A1 * | 8/2007 | Bandyopadhyay | A61F 2/28 623/23.5 |
| 2008/0161927 A1 * | 7/2008 | Savage | A61F 2/4455 623/17.16 |
| 2008/0269893 A1 | 10/2008 | Bhatnagar et al. | |
| 2008/0281346 A1 * | 11/2008 | Greenhalgh | A61B 17/8858 606/191 |
| 2009/0187249 A1 * | 7/2009 | Osman | A61B 17/7097 623/17.16 |
| 2009/0240324 A1 * | 9/2009 | Smith | A61F 2/86 623/1.42 |
| 2010/0036467 A1 | 2/2010 | Kraus | |
| 2010/0042214 A1 | 2/2010 | Nebosky et al. | |
| 2010/0094420 A1 | 4/2010 | Grohowski, Jr. | |
| 2010/0262245 A1 * | 10/2010 | Alfaro | A61F 2/4465 623/17.16 |
| 2011/0004307 A1 * | 1/2011 | Ahn | A61F 2/441 623/17.12 |
| 2011/0071635 A1 * | 3/2011 | Zhang | B32B 15/08 623/17.11 |
| 2011/0172775 A1 * | 7/2011 | Flickinger | A61F 2/4465 623/17.16 |
| 2011/0224796 A1 * | 9/2011 | Weiland | A61F 2/4455 623/17.16 |
| 2011/0301709 A1 * | 12/2011 | Kraus | A61F 2/4465 623/17.11 |
| 2012/0191188 A1 * | 7/2012 | Huang | A61F 2/447 623/17.11 |
| 2012/0271361 A1 | 10/2012 | Zhou et al. | |
| 2012/0271362 A1 | 10/2012 | Martineau et al. | |
| 2012/0330420 A1 * | 12/2012 | Brodke | A61F 2/30767 623/17.16 |
| 2013/0022943 A1 | 1/2013 | Collins et al. | |
| 2013/0090733 A1 * | 4/2013 | Kraft | A61F 2/442 623/17.16 |
| 2013/0116793 A1 * | 5/2013 | Kloss | A61F 2/442 623/17.16 |
| 2013/0178900 A1 | 7/2013 | Fallin et al. | |
| 2014/0180432 A1 | 6/2014 | Conway et al. | |
| 2015/0045903 A1 * | 2/2015 | Neal | B23K 15/0006 623/21.18 |

FOREIGN PATENT DOCUMENTS

| | | | |
|---|---|---|---|
| FR | 2827157 A1 * | 1/2003 | A61F 2/442 |
| WO | 2007/048038 A2 | 4/2007 | |
| WO | 2010025386 A1 | 3/2010 | |
| WO | 2012109748 | 8/2012 | |
| WO | 2014068259 | 5/2014 | |

* cited by examiner

SURGICAL IMPLANT WITH POROUS REGION

BACKGROUND

This disclosure relates to a surgical implant. The surgical implant includes at least one porous region that facilitates tissue ingrowth through the implant.

Orthopedic procedures are often performed to repair musculoskeletal injuries. For example, soft tissue may tear away from bone during vigorous exercise or sporting activities. When tears occur, reattachment may be necessary to repair the damaged tissue. Various surgical implants can be used to repair damaged tissue, including but not limited to screws, anchors, wedges, etc.

Many surgical implants are made from bio-absorbable materials. The bio-absorbable materials must be of sufficient strength to withstand loads encountered during the healing process and must have a chemistry that is compatible with the human body.

SUMMARY

A surgical implant according to an exemplary aspect of the present disclosure includes, among other things, a body that extends along a longitudinal axis between a drive head and a tip. The body includes a cannulation disposed about the longitudinal axis and extending from the tip to the drive head, a solid thread that wraps around the body and a porous region circumferentially extending about the body between adjacent revolutions of the solid thread.

In a further non-limiting embodiment of the foregoing surgical implant, the surgical implant is a suture anchor.

In a further non-limiting embodiment of either of the foregoing surgical implants, the surgical implant is an interference screw.

In a further non-limiting embodiment of any of the foregoing surgical implants, the porous region includes a plurality of interconnected pores.

In a further non-limiting embodiment of any of the foregoing surgical implants, the tip and the drive head are solid.

In a further non-limiting embodiment of any of the foregoing surgical implants, a porous extension extends from the porous region to the cannulation.

In a further non-limiting embodiment of any of the foregoing surgical implants, a vent connects between the cannulation and the porous region.

In a further non-limiting embodiment of any of the foregoing surgical implants, the body includes an inner wall that circumscribes the cannulation, the inner wall being solid.

In a further non-limiting embodiment of any of the foregoing surgical implants, a solid strut connects between the solid thread and the cannulation.

In a further non-limiting embodiment of any of the foregoing surgical implants, the solid thread includes a minor diameter and a major diameter, and the solid thread is completely solid between the minor diameter and the major diameter.

In a further non-limiting embodiment of any of the foregoing surgical implants, the body and the porous region are made of the same material.

In a further non-limiting embodiment of any of the foregoing surgical implants, the porous region is disposed in a portion of the body that extends between the cannulation and the solid thread.

A surgical implant according to another exemplary aspect of the present disclosure includes, among other things, a body that extends along a longitudinal axis between a drive head and a tip. The body includes a cannulation disposed along the longitudinal axis and extending from the tip to the drive head, the cannulation circumscribed by an inner wall. A solid thread spirals about the body between the drive head and the tip, the solid thread being completely solid between a minor diameter and a major diameter. A porous region includes a plurality of interconnected pores that are formed between adjacent revolutions of the solid thread. A solid strut connects between the solid thread and the inner wall.

In a further non-limiting embodiment of the foregoing surgical implant, a vent is formed through the inner wall.

In a further non-limiting embodiment of either of the foregoing surgical implants, the porous region includes a porous extension that extends to the inner wall.

In a further non-limiting embodiment of any of the foregoing surgical implants, the porous region includes a height that extends across at least two of the revolutions of the solid thread.

A surgical implant according to another exemplary aspect of the present disclosure includes, among other things, a body extending between an inner wall an outer wall and at least one porous region that extends continuously around the body between the inner wall and the outer wall.

In a further non-limiting embodiment of the foregoing surgical implant, the surgical implant is a wedge that includes a plurality of porous regions disposed in the body. Each porous region of the plurality of porous regions connects to an adjacent porous region of the plurality of porous regions.

In a further non-limiting embodiment of either of the foregoing surgical implants, the plurality of porous regions extend continuously through the body to establish an uninterrupted network of interconnected pores inside the body.

In a further non-limiting embodiment of any of the foregoing surgical implants, the plurality of porous regions connect to one another through vents formed in the inner wall, the outer wall and solid struts of the body.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure describes surgical implants, such as screws, suture anchors, or wedges, which can be used to repair musculoskeletal injuries. The surgical implants include porous regions that facilitate tissue ingrowth subsequent to fixation of the implant within bone. In some embodiments, the surgical implant includes solid struts that increase the strength and stability of the implant near the porous regions. In other embodiments, the surgical implant includes vents formed through walls of the implant. These and other features of this disclosure are described in greater detail in the paragraphs that follow.

Figure 1:
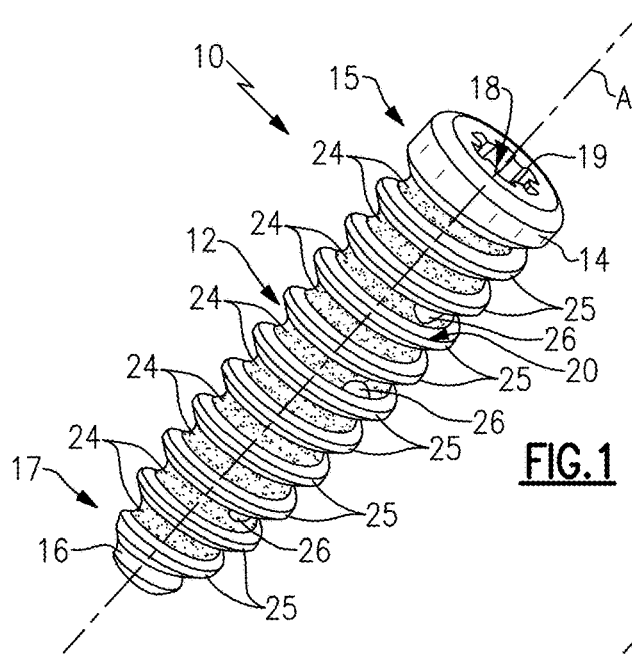
FIG. 1 illustrates a surgical implant according to a first embodiment of this disclosure.
Figure 2:
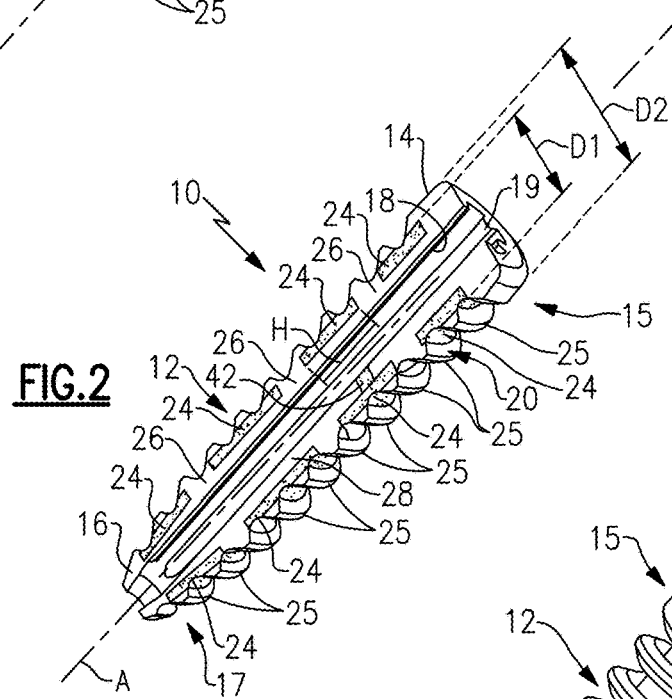
FIG. 2 is a cross-sectional view of the surgical implant of FIG. 1.
Figure 3:
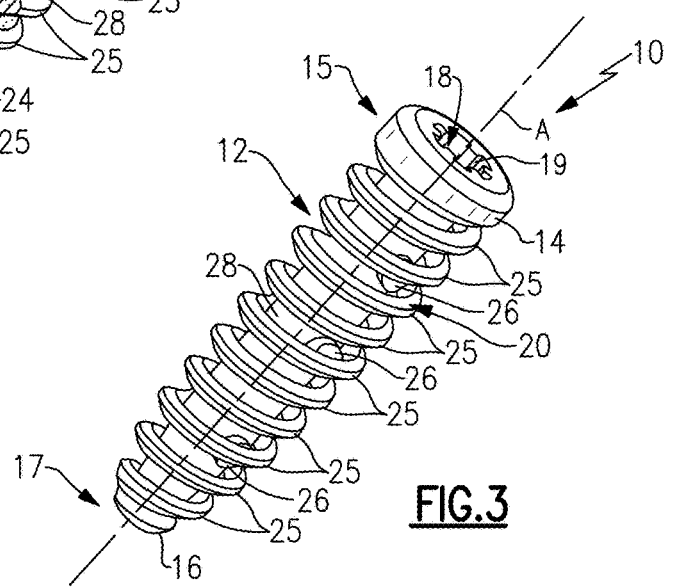
FIG. 3 illustrates the surgical implant of FIG. 1 with the porous regions of the implant removed.

A surgical implant 10 is illustrated in FIGS. 1, 2 and 3. The surgical implant 10 is configured for use in various soft tissue repairs and may be fixated within bone to attach tissue (e.g., ligament, tendon, graft, etc.) to the bone. In one non-limiting embodiment, the surgical implant 10 is an interference screw that can be used in conjunction with a variety of orthopedic surgical repairs, such as an ACL reconstruction. Of course, this disclosure is not limited to interference screws or to ACL reconstructions and could have various additional implementations within the scope of this disclosure.

The exemplary surgical implant 10 includes a body 12 that extends along a longitudinal axis A between a drive head 14, formed at a proximal end 15, and a tip 16, formed at a distal end 17. The drive head 14 and the tip 16 are both solid portions (i.e., substantially non-porous) of the surgical implant 10. The body 12 may or may not taper between the drive head 14 and the tip 16. The size and shape of the body 12 are not intended to limit this disclosure.

The drive head 14 may accommodate a driver for insertion of the surgical implant 10 into bone. In one non-limiting embodiment, the drive head 14 includes a hex opening 19 for receiving a corresponding hex-head of a driver (not shown). The drive head 14 could include other configurations and is not limited to the hex shape.

The tip 16 may be shaped in any manner to facilitate insertion of the surgical implant 10 into bone. For example, the tip 16 may be blunted, rounded, pointed, or otherwise shaped.

The body 12 additionally includes a cannulation 18 that extends from the tip 16 to the drive head 14 (best shown in FIG. 2). The cannulation 18 may be circumferentially disposed about the longitudinal axis A. The cannulation 18 establishes a passage through the body 12 for accommodating a guide pin, wire or shaft.

A solid thread 20 wraps around the body 12, such as in a helical pattern, between the drive head 14 and the tip 16. In one embodiment, the solid thread 20 spirals around the body 12 and includes a plurality of revolutions 25. The solid thread 20 includes a minor diameter D1 and a major diameter D2 (see FIG. 2). The dimension of the minor diameter D1 and the major diameter D2, as well as thread pitch and other properties associated with the solid thread 20, are not intended to limit this disclosure. The solid thread 20 could also be either a continuous or a discontinuous thread. In one embodiment, the solid thread 20 is completely solid, or substantially non-porous, between the minor diameter D1 and the major diameter D2.

One or more porous regions 24 may be formed in the body 12 of the surgical implant 10. Each porous region 24 includes a plurality of interconnected pores (see, for example, FIG. 4). The porous regions 24 establish areas of increased porosity that facilitate tissue ingrowth subsequent to implantation of the surgical implant 10 into bone.

The porous regions 24 may be provided in selected regions of the body 12. For example, the porous regions 24 may circumferentially extend about the body 12 between adjacent revolutions 25 of the solid thread 20. In one embodiment, the porous regions 24 are formed in the body 12 between the cannulation 18 and the solid thread 20. In another embodiment, the porous regions 24 extend from the minor diameter D1 toward the cannulation 18. Some of the porous regions 24 may include a height H that extends across multiple revolutions 25 of the solid thread 20 (see FIG. 2). Other configurations are also contemplated.

In another non-limiting embodiment, one or more solid struts 26 connect solid sections of the surgical implant 10. For example, the solid struts 26 may extend between the solid thread 20 and the cannulation 18. The solid struts 26 increase the strength and stability of the body 12 of the surgical implant 10 near the porous regions 24. In one embodiment, the solid struts 26 are generally cylindrical shaped.

In one embodiment, the surgical implant 10 may be made of a bio-absorbable polymer. Non-limiting examples of suitable materials include poly-L-lactide (PLLA), poly lactic acid (PLDLA), PLLA with biphasic calcium phosphate, or PLDLA with hydroxyapatite plus biphasic calcium phosphate. Other exemplary materials may include thermosets, thermoplastics, bio-absorbable materials comprised of a single polymer, blend, or composites made of multiple materials, multiple polymers, fibers with polymer or granules/powder with polymer. Other materials are also contemplated within the scope of this disclosure. In another embodiment, the body 12 and the porous regions 24 of the surgical implant are made of the same material.

The porous regions 24 may be formed in the bio-absorbable polymer that makes up the surgical implant 10 using a variety of techniques. In one non-limiting technique, the porous regions 24 are formed by merging granules of polyvinyl alcohol (PVA) with the bio-absorbable polymer, curing the PVA together with the bio-absorbable polymer, and then dissolving the PVA granules out of the bio-absorbable polymer. Other techniques for forming the porous regions 24 may alternatively or additionally be utilized.

Referring now to FIG. 2 and FIG. 3 (which illustrates the surgical implant 10 with the porous regions 24 removed for clarity), the body 12 may include an inner wall 28. The inner wall 28 circumscribes the cannulation 18. The solid struts 26 may extend from the inner wall 28 to the solid thread 20. In another embodiment, the porous regions 24 include a porous extension 42 that extends through the inner wall 28 for further facilitating tissue ingrowth (see, for example, FIG. 2).

Figure 4:
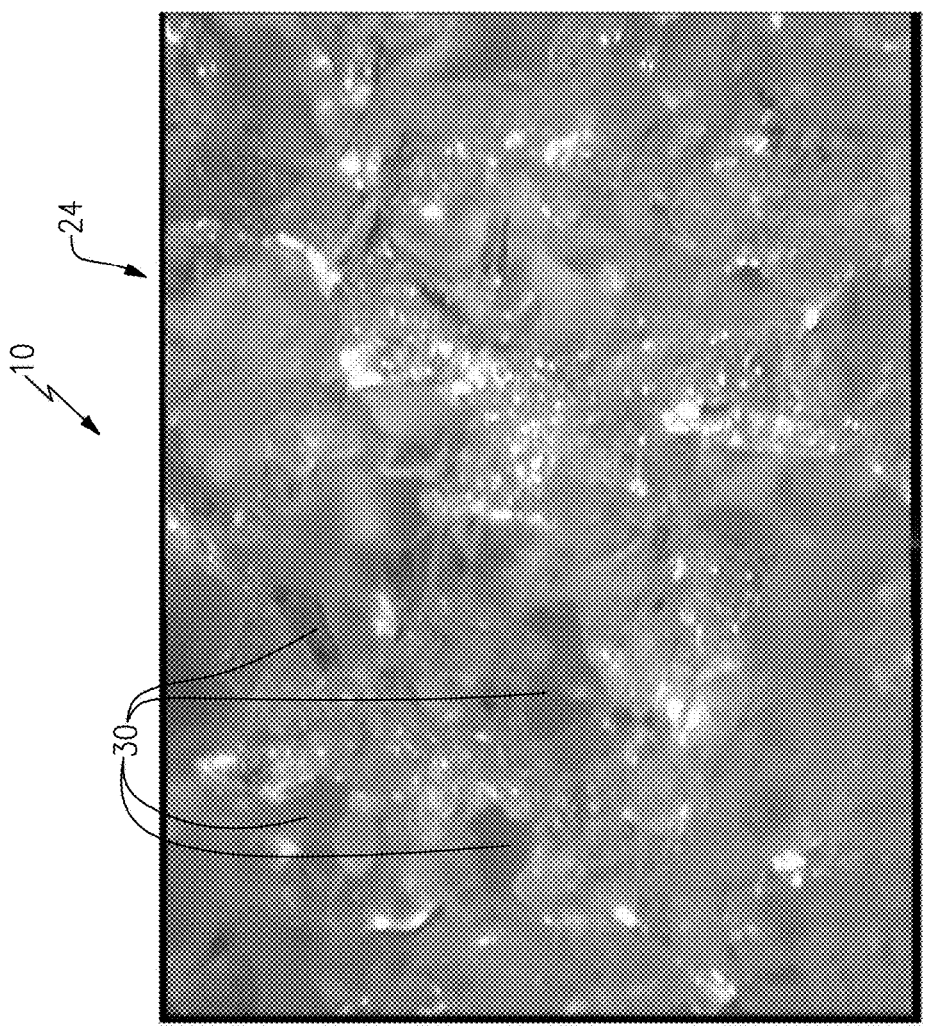
FIG. 4 illustrates a magnified view of a porous region of a surgical implant.

FIG. 4 illustrates a magnified view of a porous region 24 of the surgical implant 10. The porous region 24 includes a plurality of interconnected pores 30. The interconnected pores 30 can be controlled to any desired size and shape and may be formed at any desired location within the surgical implant 10 to facilitate tissue ingrowth.

Figure 5:
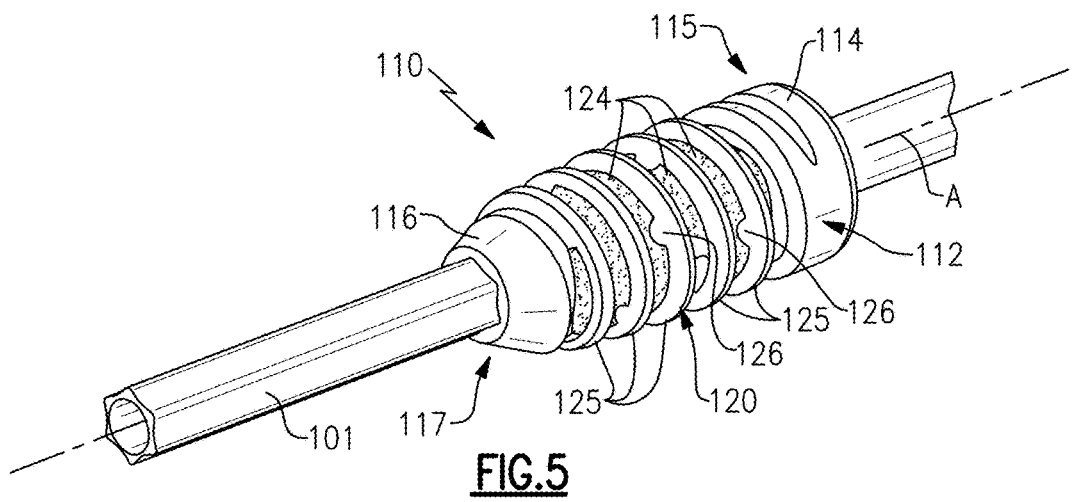
FIG. 5 illustrates a surgical implant according to a second embodiment of this disclosure.
Figure 6:
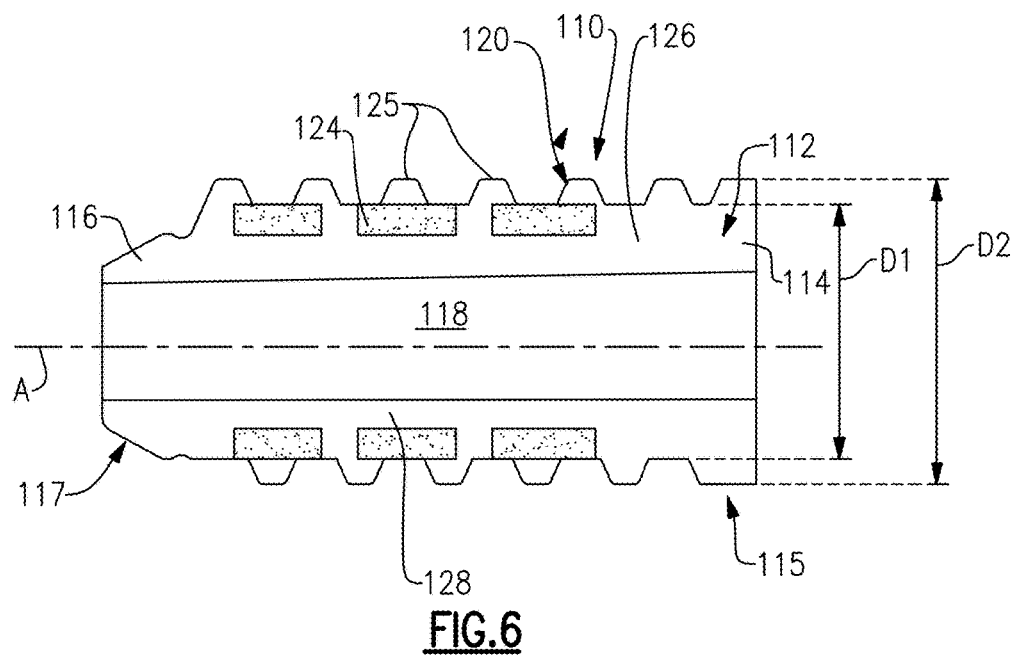
FIG. 6 is a cross-sectional view of the surgical implant of FIG. 5.

FIGS. 5 and 6 illustrate another surgical implant 110. In this embodiment, like reference numerals designate like elements where appropriate and reference numerals with the addition of 100 or multiples thereof designate modified elements that are understood to incorporate the same features and benefits of the corresponding original elements.

In this embodiment, the surgical implant 110 is a suture anchor that can be used to attach tissue to bone as part of a rotator cuff repair, Achilles tendon repair, patellar tendon repair, ACL/PCL reconstruction, hip and shoulder reconstructions, or any other orthopedic repair. The surgical implant 110 includes a body 112 that extends along a longitudinal axis A between a drive head 114, formed at a proximal end 115, and a tip 116, formed at a distal end 117.

A cannulation 118 (see FIG. 6) extends from the tip 116 to the drive head 114. The cannulation 118 may be circumferentially disposed about the longitudinal axis A. The cannulation 118 establishes a passage through the body 112 for accommodating a shaft 101, which may be part of a driver, for example.

A solid thread 120 wraps around the body 112 between the drive head 114 and the tip 116. The solid thread 120 is completely solid between a minor diameter D1 and a major diameter D2 (see FIG. 6). One or more porous regions 124 may be formed in the body 112 of the surgical implant 110. The porous regions 124 may circumferentially extend about the body 112 between adjacent revolutions 125 of the solid thread 120. In one embodiment, the porous regions 124 are formed in the body 112 between the cannulation 118 and the solid thread 120.

One or more solid struts 126 may connect solid sections of the surgical implant 110. For example, the solid struts 126 may extend between the solid thread 120 and an inner wall 128 of the body 112 that circumscribes the cannulation 118.

Figure 7:
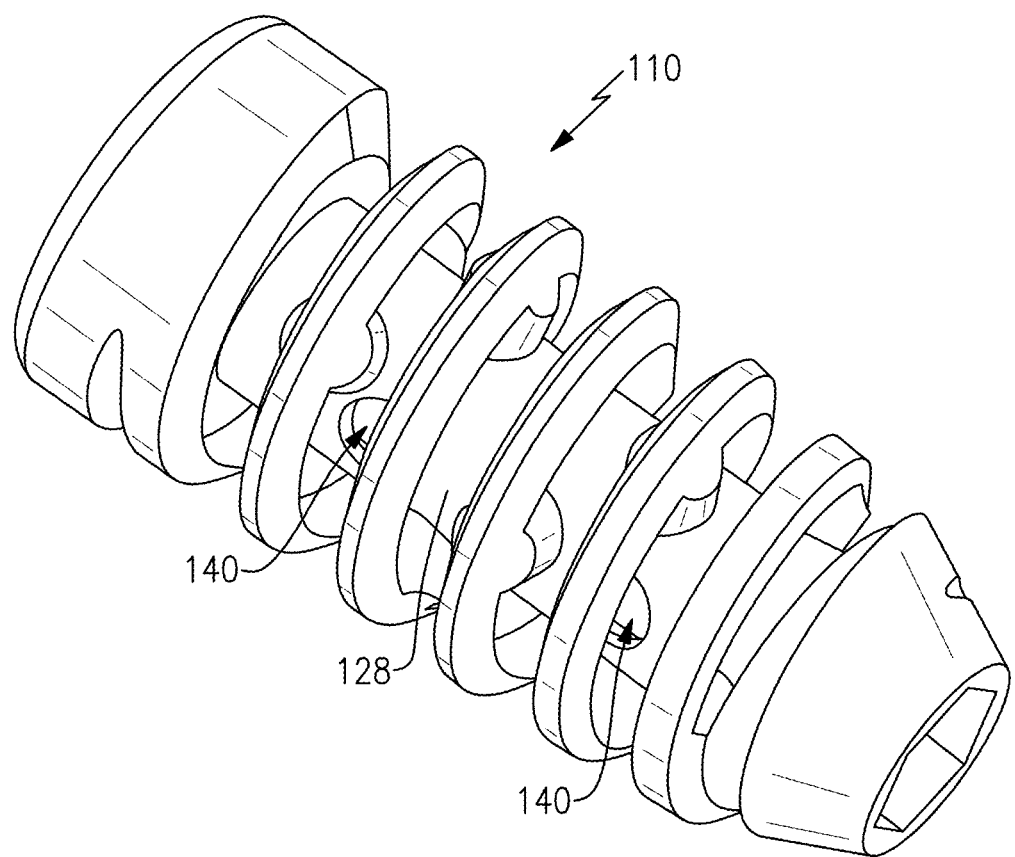
FIGS. 7 and 8 illustrate the surgical implant of FIG. 5 with the porous regions of the implant removed.
Figure 8:
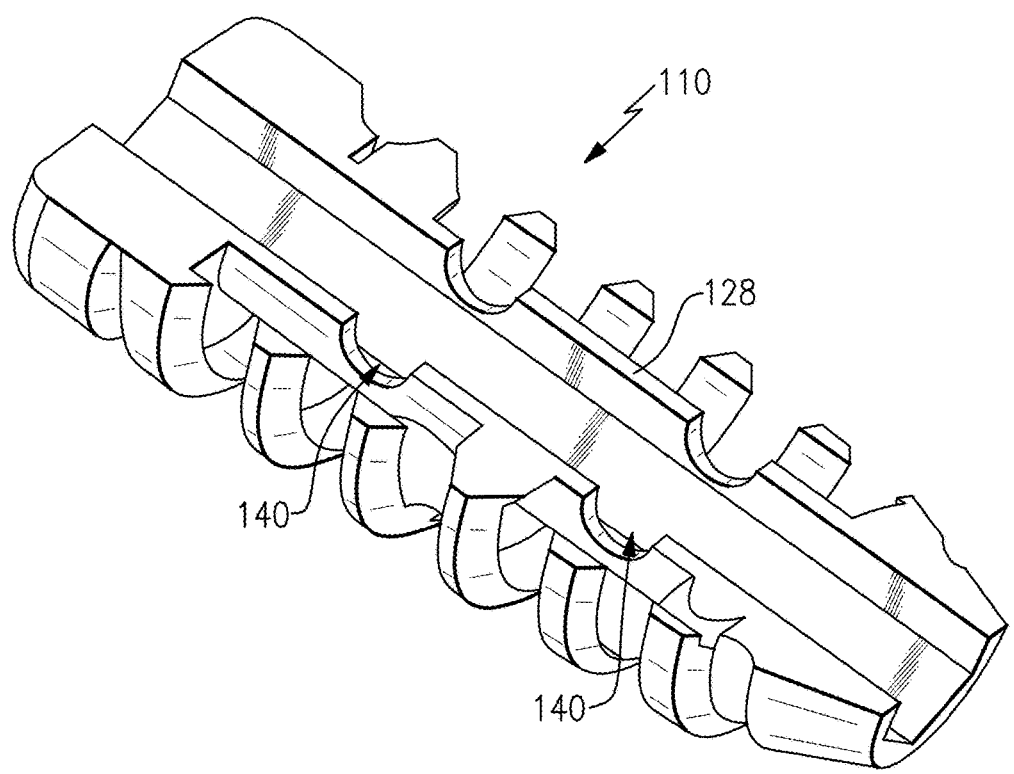

Referring to FIGS. 7 and 8, one or more vents 140 may be formed through the inner wall 128. The vents 140 may facilitate tissue ingrowth through the surgical implant 110. The porous regions 124 have been removed from FIGS. 7 and 8 to better illustrate the vents 140.

Figure 9:
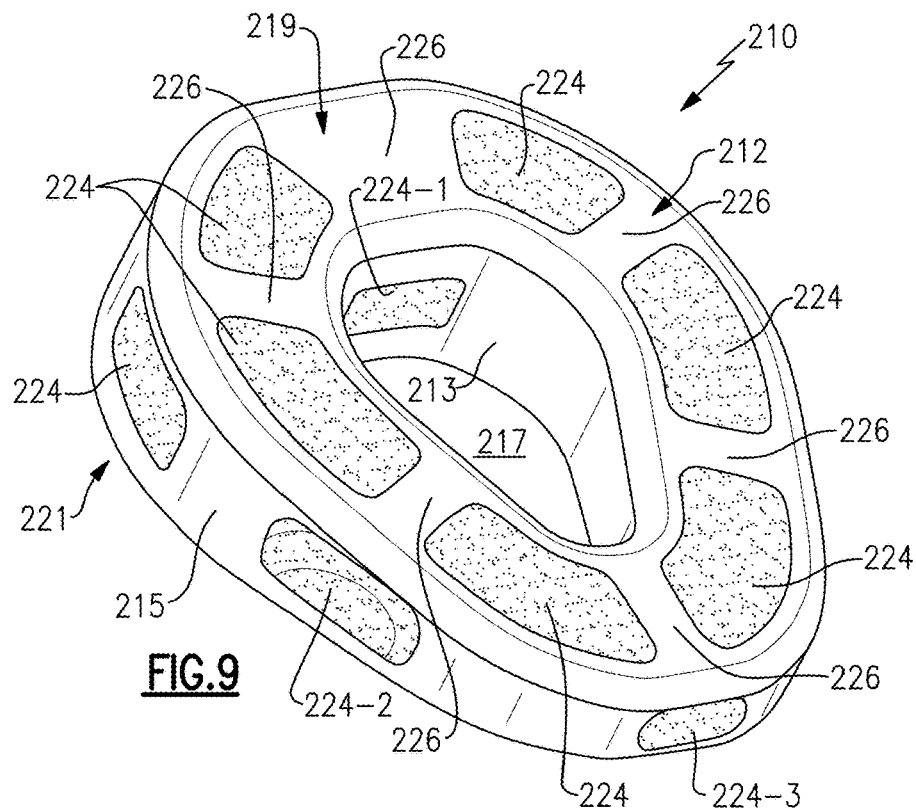
FIG. 9 illustrates a surgical implant according to yet another embodiment of this disclosure.
Figure 10:
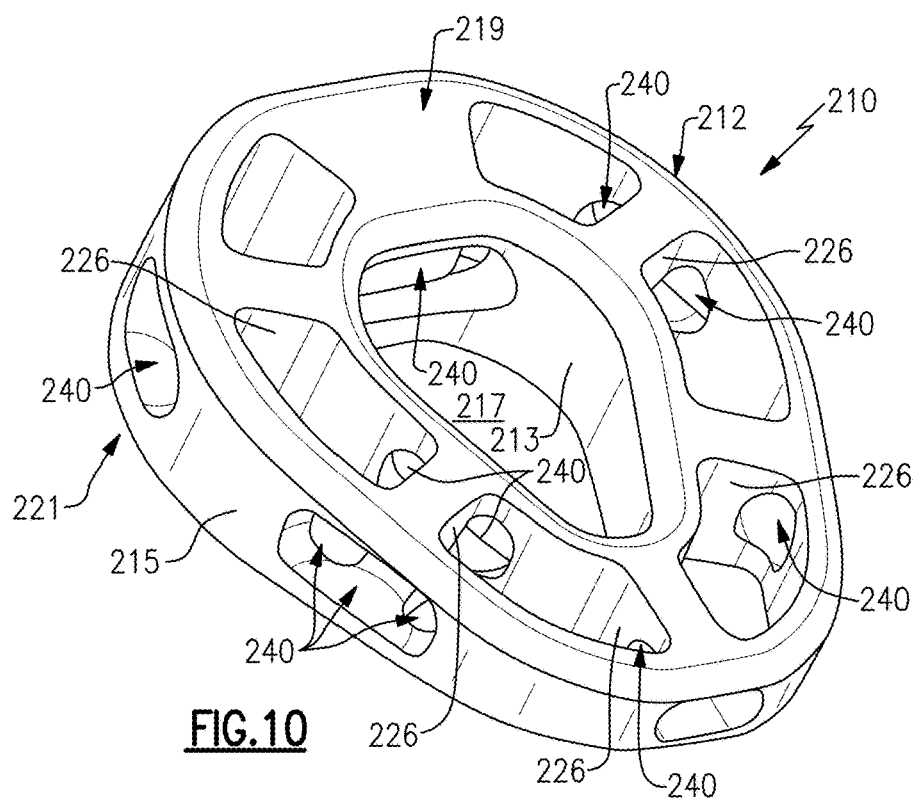
FIG. 10 illustrates the surgical implant of FIG. 9 with the porous regions of the implant removed.
Figure 11:
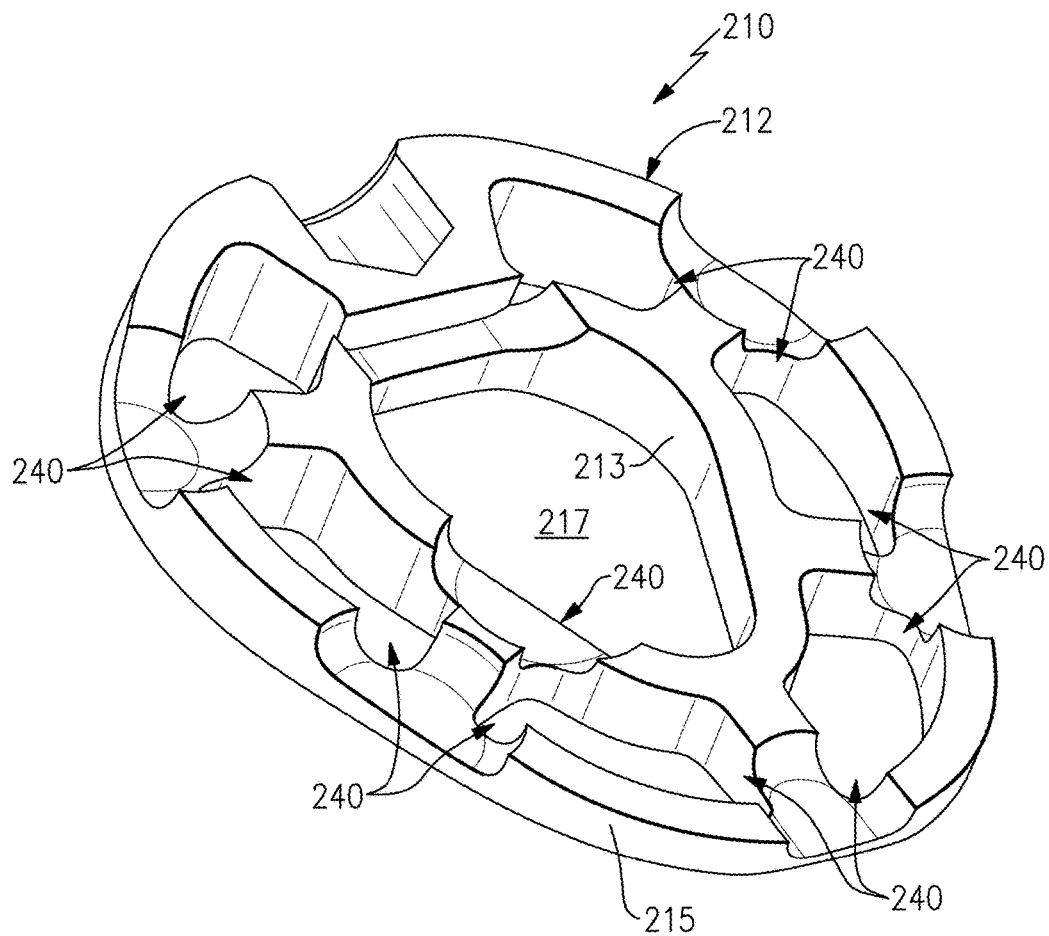
FIG. 11 is a cross-sectional view of the surgical implant of FIG. 10.

FIGS. 9, 10 and 11 illustrate yet another surgical implant 210. In this embodiment, the surgical implant 210 is a wedge, such as an osteotomy wedge, that can be used to repair a bone deformity. For example, the surgical implant 210 can be implanted during an osteotomy procedure to repair a deformity associated with a knee, ankle, foot or other joint.

The surgical implant 210 includes a body 212 that can include any size and any shape. In one non-limiting embodiment, the body 212 extends between an inner wall 213 and an outer wall 215 that is spaced from the inner wall 213. The outer wall 215 may circumscribe the inner wall 213. A central bore 217 may extend through the body 212 inside of the inner wall 213. A top face 219 and a bottom face 221 of the body 212 may extend between the inner wall 213 and the outer wall 215.

One or more porous regions 224 may be formed in the body 212 of the surgical implant 210 (see FIG. 9). Each porous region 224 includes a plurality of interconnected pores that establish areas of increased porosity that facilitate tissue ingrowth subsequent to implantation of the surgical implant 210 into bone. The central bore 217 may further facilitate tissue ingrowth. In one embodiment, at least one continuous porous region 224 extends continuously around the body 212 between the inner wall 213 and the outer wall 215. In other embodiments, some of the porous regions 224 may extend through the inner wall 213 (see, for example, the porous region 224-1) and/or the outer wall 215 (see, for example, the porous regions 224-2, 224-3).

In another non-limiting embodiment, one or more solid struts 226 connect between solid sections of the surgical implant 210. For example, the solid struts 226 may extend between solid portions of the inner wall 213 and the outer wall 215 and between solid portions of the top face 219 and the bottom face 221. The solid struts 226 increase the strength and stability of the body 212 of the surgical implant 210 near the porous regions 224. In one embodiment, the porous regions 224 are at least partially separated from one another by the solid struts 226.

As best shown in FIGS. 10 and 11, which illustrate the surgical implant 210 with the porous regions 224 removed, vents 240, or openings, may be formed through both the inner wall 213 and the outer wall 215. Some of the vents 240 could also extend through the solid struts 226. In one embodiment, adjacent porous regions 224 of the surgical implant 210 connect with one another via the vents 240 to establish a continuous area of porosity distributed through the entirety of the body 212. Stated another way, the porous regions 224 may extend continuously through the body 212 to establish an uninterrupted network of interconnected pores inside the body 212. Therefore, the porous regions 224 may not be discrete regions of the body 212 that are isolated from other porous regions 224.

The porous regions of the various surgical implants of this disclosure are exemplary only and are not intended to limit this disclosure. The surgical implants may be designed to include more or less porosity within the scope of this disclosure.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. An osteotomy wedge for repairing a bone deformity, comprising:
 a body extending between an annular inner wall and an annular outer wall that circumscribe said inner wall, said body having a flat, non-porous top face and a flat, non-porous bottom face that extend between said inner wall and said outer wall, wherein the flat top face and flat bottom face taper towards each other to form a wedge shape, wherein the outer wall forms side walls between the flat top face and flat bottom face of the body, wherein a top side wall and a bottom side wall are formed along a latitudinal axis of the body and said top side wall and bottom side wall are parallel to each other, and wherein two opposite sides walls are formed along a longitudinal axis of the body and said two sides walls taper towards each other;

a plurality of porous regions between said inner wall and said outer wall and between said top face and bottom face, wherein said plurality of porous regions extend continuously through said body to establish an uninterrupted network of interconnected pores inside said tapered, wedge shaped body;

a plurality of solid struts, each of the solid struts extending linearly from said inner wall to said outer wall to connect said inner wall to said outer wall, such that the plurality of porous regions are partially compartmentalized by the outer wall, the inner wall, and the solid struts; and a plurality of vents formed in said inner wall, said outer wall, and said solid struts, wherein said inner wall circumscribes an oblong central bore that extends through the top face and the bottom face of said body, and said oblong central bore is larger than each pore of said plurality of porous regions, wherein said plurality of porous regions connect to one another through said plurality of vents, wherein the plurality of solid struts extend between solid portions of the inner wall and the outer wall and between solid portions of the top face and the bottom face, wherein each of the flat top face and flat bottom face defines a bone-contacting surface.

2. The osteotomy wedge as recited in claim 1, wherein at least one of said plurality of porous regions extends through at least one of said top face and said bottom face.

3. The osteotomy wedge as recited in claim 1, wherein at least one of said plurality of porous regions extends through at least one of said inner wall and said outer wall.

4. The osteotomy wedge as recited in claim 1, wherein at least one porous region is at least partially separated from a second porous region by a solid strut.

5. The osteotomy wedge as recited in claim 1, wherein said inner wall, said outer wall, said top face, and said bottom face establish a shell for housing said plurality of porous regions.

6. The osteotomy wedge as recited in claim 1, wherein said plurality of porous regions is exposed through each of said inner wall, said outer wall, said top face, and said bottom face.

7. The osteotomy wedge as recited in claim 1, wherein said central bore is teardrop shaped.

* * * * *